United States Patent [19]

Fare et al.

[11] Patent Number: 4,791,064
[45] Date of Patent: Dec. 13, 1988

[54] PLASMIDS FROM NOCARDIA

[75] Inventors: Louis R. Fare, LaFayette Hill; Yong K. Oh, Phoenixville; Dean P. Taylor, King of Prussia; Jenifer B. Widger, Graterford, all of Pa.

[73] Assignee: SmithKline Beckman Corporation, Philadelphia, Pa.

[21] Appl. No.: 744,098

[22] Filed: Jun. 12, 1985

Related U.S. Application Data

[63] Continuation-in-part of Ser. No. 511,595, Jul. 7, 1983, abandoned.

[51] Int. Cl.$^4$ .................. C12N 1/20; C12N 1/00; C12N 15/00; C12P 21/02
[52] U.S. Cl. .................. 435/252.3; 435/320; 435/172.3; 435/70; 435/252.35; 935/29
[58] Field of Search .............. 435/172.3, 253, 317, 435/68, 20, 320; 935/29

[56] References Cited

U.S. PATENT DOCUMENTS

| | | |
|---|---|---|
| 3,067,099 | 9/1955 | McCormick et al. . |
| 4,273,875 | 6/1981 | Manis et al. . |
| 4,393,137 | 7/1983 | Manis et al. ............ 435/172.3 |
| 4,416,994 | 11/1983 | Nakatsukasa et al. ............ 435/172.3 |
| 4,460,693 | 7/1984 | Toyama et al. . |

OTHER PUBLICATIONS

Kirby et al., *Fems Microbiology Letters*, 27, 57–59 (1985).
Reh et al., *J. of Gen. Micro.*, 126, 327–336 (1981).
Birnboim et al., *Nucl. Acids Res.*, 7, 1513–1523 (1979).
Chater et al., *Curr. Top. Micro. Immunol.*, 96, 69–95 (1985).
Hayakawa et al., *J. Antibiot.*, 32(12), 1348–1350 (1979).

*Primary Examiner*—Alvin E. Tanenholtz
*Attorney, Agent, or Firm*—Carol G. Canter; Edward T. Lentz; Alan D. Lourie

[57] ABSTRACT

A plasmid naturally present in *N. orientalis* can be used as a vector for cloning or expression in Actinomycetales and to derive other vectors.

17 Claims, 3 Drawing Sheets

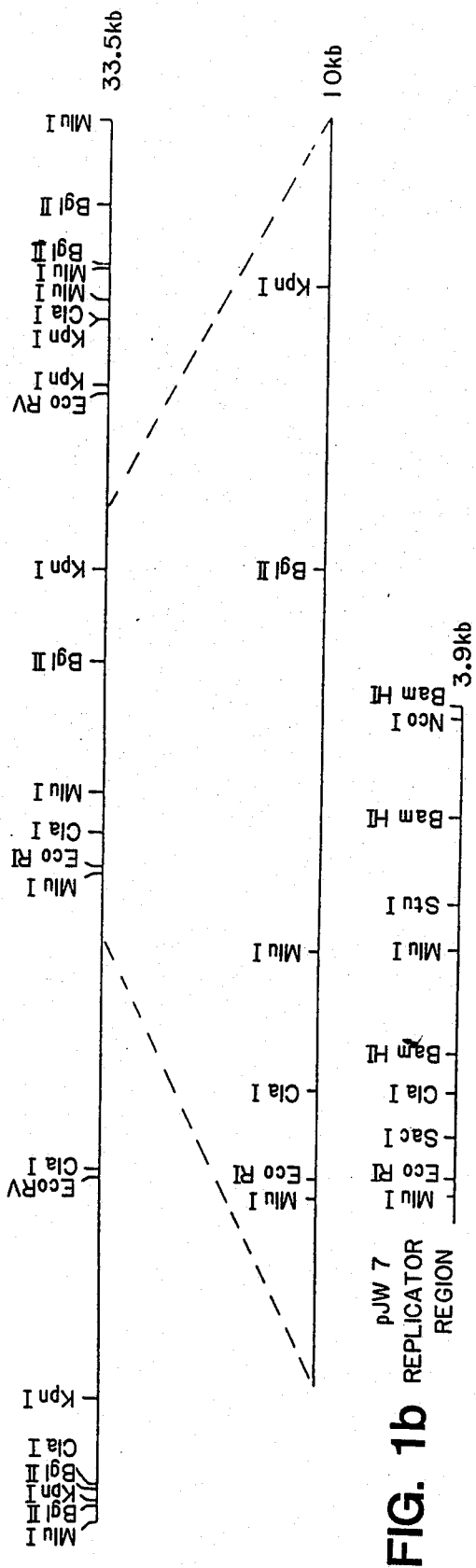
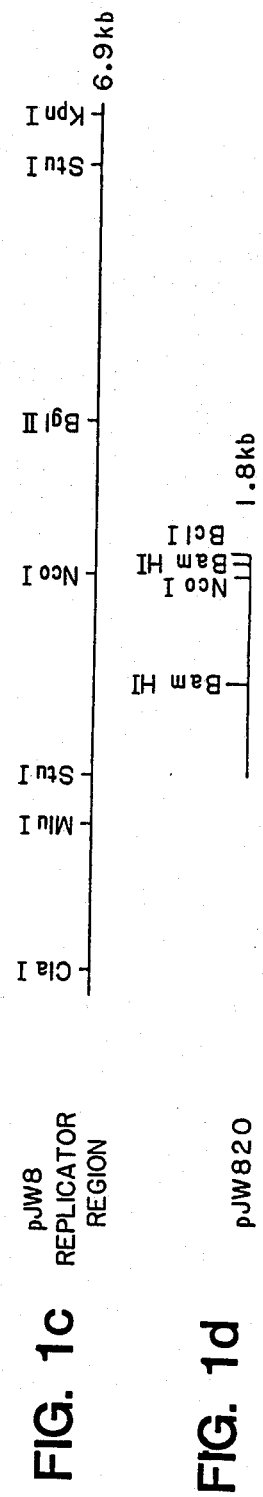

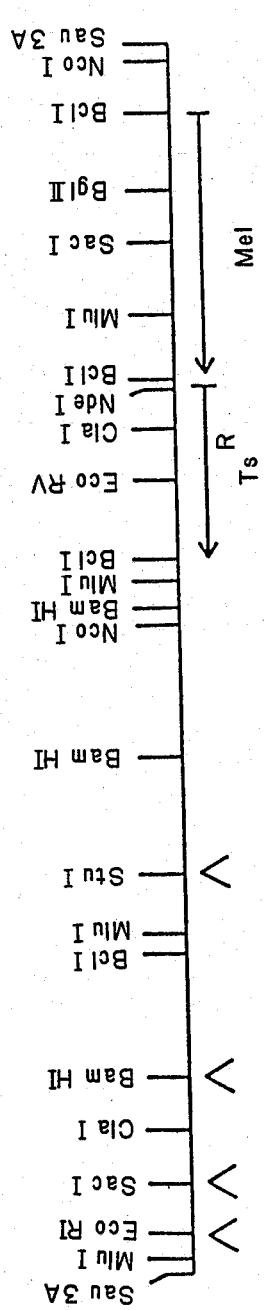
FIG. 2a  pJW7  7.1kb
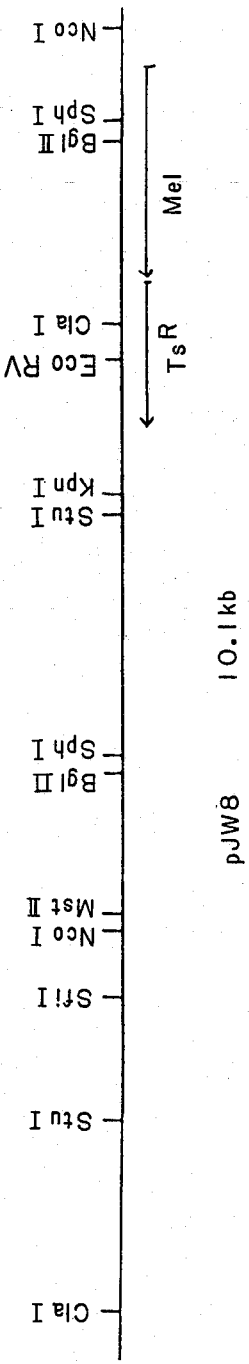
FIG. 2b  pJW8  10.1kb

PLASMIDS FROM NOCARDIA

CROSS REFERENCES TO RELATED APPLICATIONS

This application is a continuation-in-part of Ser. No. 511,595 filed July 7, 1983 and now abandoned.

BACKGROUND OF THE INVENTION

This invention relates to a plasmid naturally present in *Nocardia orientalis* and use thereof as a vector and to derive other vectors.

A vector used in expression or cloning as an autonomous unit contains a functional region which allows the vector to replicate autonomously in host cells. Such regions are referred to as replicons or autonomously replicating segments. Known vectors are derived from naturally occurring molecules, often double stranded DNA plasmids. Such molecules can be used as a source of functional regions, including replicons, genes expressing desired products including products which confer phenotypically selectable traits, and transcription and translation regulatory regions.

Plasmids carrying regions which function in members of the Order Actinomycetales, and especially of the Family Streptomycetaceae, are of interest because of the large number of products, particularly secondary metabolites such as antibiotics, which are produced by the Actinomycetales. Such plasmids can serve as sources of functional regions for use in genetic engineering of Actinomycetales.

Techniques useful in genetic engineering of Streptomycetacease are reviewed by Chater et al. in *Current Topics in Microbiology and Immunology* 96: 69–95 (1982), which is incorporated by reference herein as though fully set forth. Such techniques are now generally well known and have resulted in the finding of several plasmids and other vectors useful in genetic engineering of Actinomycetales.

For example, Chater et al., cited above, report three families of Streptomyces plasmids. These are represented by SCP2, SLP1 and pIJ101. Bibb et al., *Mol. Gen. Genet.* 184: 230–240 (1981) and U.S. Pat. No. 4,360,597, report that SLP1 resulted from excision of a fragment of *S. coelicolor* A3(2) chromosomal DNA upon crossing with *S. lividans* 66.

Other families of Streptomyces vectors derived from naturally-occurring plasmids or from excision of chromosomal DNA have been reported. Additionally, various derivatives of Streptomyces vectors are known, including hybrid vectors. For example, Schottel et al., *J. Bacteriol.* 146: 360–368 (1981), describe construction of hybrid plasmids carrying *E. coli* and streptomyces replicons.

Many conjugative Streptomyces plasmids, including the SCP2, SLP1 and PIJ101 plasmids, cause a lethal zygosis-like phenomenon when a plasmid-bearing strain is crossed with a non-plasmid-bearing strain such as *S. lividans* 1326. This property can be useful as a test for presence of plasmids in Streptomyces. See, Hopwood et al., "Microbiology 1981", edit. by Schlessinger, Am. Soc. Microbiol., Washington, D.C. 1981, pp. 367–370.

Hopwood et al., *Bacteriol. Rev.* 41(3): 595–635 (1979); Akagawa et al., *J. Antibiot.* 32(6): 610–620 (1979); Hayakawa et al., *J. Antibiot.* 32(12): 1348–1350 (1979); and Toyama et al., *J. Antibiot.* 35(3): 369–373 (1982) report plasmid involvement in antibiotic synthesis in a variety of Streptomyces sp.

Vancomycin production by strains of *N. orientalis* has been reported, for example, by McCormick et al., *Antibiotics Annual* 1955/56, pp. 606–611, Pittenger et al., *Antibiot. Chemother.* 6(11): 642–647 (1956), U. K. Specification No. 795,289 and McCormick et al., U.S. Pat. No. 3,067,099.

Reh et al., *J. Gen. Micro.*, 126, 327–336 (1981) disclose genetic evidence that suggests the presence of a conjugative plasmid in *Nocardia opaca* strain lb. Reh et al. do not disclose the physical isolation or characterization of such a plasmid.

SUMMARY OF THE INVENTION

This invention relates to a plasmid, naturally present in *Nocardia orientalis*, isolated from its natural host, and mutants and genetically engineered derivatives thereof. Preferably the plasmid is one which is naturally present in *N. orientalis* strain NRRL 2452, i.e. pSO408, and mutants and genetically engineered derivatives thereof.

More preferably the vector is one which is derived from pSO408, such as pYO33, and mutants and genetically engineered derivatives thereof. Most preferably, the vector is derived from pYO33, such as vector pJW7, vector pJW8, vector pJW8D, vector pJW81, vector pJW811, vector pJW815, vector pJW817, vector pJW820, vector pJW86, vector pJW81EM or any other vector comprising a functional region of any of the plasmids of the invention.

Yet another aspect of this invention is a host microorganism transformed with a naturally occurring plasmid or derivative vector of this invention, provided that the host microorganism is other than a natural host for the plasmid.

The final aspect of this invention relates to a method of expressing a functional DNA sequence derived from Nocardia, other actinomycetes, viruses, other organisms or cells, which comprises (a) transforming a host microorganism with a naturally occurring plasmid or derivative vector of this invention which also contains the functional DNA sequence; and (b) culturing the transformed host in an appropriate medium.

BRIEF DESCRIPTION OF THE DRAWINGS

FIG. 1(a) is a restriction endonuclease cleavage map of pYO33.

FIG. 1(b) is a restriction endonuclease cleavage map of the pJW7 replicator region.

FIG. 1(c) is a restriction endonuclease cleavage map of the pJW8 replicator region.

FIG. 1(d) is a restriction endonuclease cleavage map of the pJW820 replicator region.

FIG. 2(a) is a restriction endonuclease cleavage map of pJW7.

FIG. 2(b) is a restriction endonuclease cleavage map of pJW8.

DETAILED DESCRIPTION OF THE INVENTION

Figure 3A:
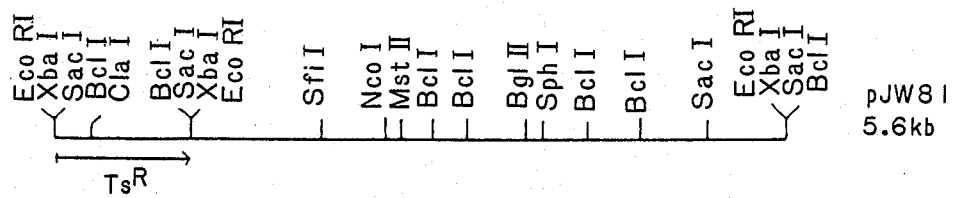
FIG. 3(a) is a restriction endonuclease cleavage map of pJW81.

By "replicator region" is meant that region of a plasmid which comprises functions involved in, and necessary for, replication of the plasmid as a stable, autonomous episome.

*Nocardia orientalis* was first reported as *Streptomyces orientalis* by McCormick et al., *Antibiotics Annual*, 606-611 (1955-56) and Pittenger et al., *Antibiotics and Chemotherapy*, VI (11), 642-647 (1956). The taxonomic positioning of *Nocardia orientalis* as a member of the genus Nocardia instead of the genus Streptomyces was reported by Rautenshtein et al., *Microbiology*, 44(3), 467-471 (1975), based on their evaluation of the microorganism's micromorphology, growth cycle, cell wall chemical composition, and sensitivity to a lysozyme and specific phages from related proactinomycetes. The genus Nocardia is also known as Proactinomyces and the genus Streptomyces is also known as Antinomyces. Therefore, as used herein, the term "*Nocardia orientalis*" is synonymous with the terms Streptomyces orientalis, Proacetinomyces orientalis or Actinomyces orientalis.

A plasmid naturally present in *Nocardia orientalis* can be isolated from its natural host by known techniques including, for example, the techniques reported by Chater et al., *Current Topics in Microbiology and Immunology* 96: 69-95 (1982), Bibb, *Mol. Gen. Genet.* 154: 155-166 (1977), Birnboim et al., *Nucl. Acids Res.* 7: 1513-1523 (1979), and Kieser, *Plasmid*, 12, 19-36 (1984).

pSO408 was originally isolated from *N. orientalis* strain NRRL 2452. The NRRL 2452 strain is one of three vancomycin-producing strains described by McCormick et al., in U.S. Pat. No. 3,067,099. The strain is slightly arsenate resistant (resistant to 2 mM sodium arsenate) and vancomycin resistant. The other strains reported by McCormick et al., NRRL 2450 and NRRL 2451, have not been found to contain any naturally occurring plasmids. NRRL 2452 is publicly available from various sources, such as from the American Type Culture Collection, Rockville, Md., U.S.A., under the accession number ATCC 19795.

Vector pYO33 is an example of a vector derived directly from a naturally occurring plasmid of this invention. pYO33 is a mutant of pSO408, and was prepared by arsenate-stressing a culture of strain NRRL 2452, wherein said arsenate-stressed strain is hereinafter referred to as strain V33, and then isolated pYO33 from strain V33. pYO33 is a higher copy number vector, i.e., it is carried by strain V33 in higher copy number (~110 per chromosome equivalent) than the naturally occurring plasmid, pSO408, is carried (~70 per chromosome equivalent), in NRRL 2452.

The pYO33 DNA is 33.5 kilobase pairs (kb) ±3%. It can be used as a cloning or expression vector but, because of its size, is preferbly used as a source of a functional region, especially its replicon, for construction of derivative cloning or expression vectors. An illustrative restriction site and functional map of pYO33 is presented in FIG. 1(*a*). For purposes of the present application, neither FIG. 1(*a*) nor any of the subsequent figures are drawn to scale. Table I substantially shows the numbers of restriction sites in pYO33 for various tested restriction endonucleases.

TABLE I

| Restriction Endonuclease | Number[a] of Sites | Restriction Endonuclease | Number of Sites |
|---|---|---|---|
| BamHI | 17 | NcoI | 5 |
| BclI | 10 | NruI | 11 |
| BglII | 4 | PstI | 20 |
| BssHII | 7 | PvuI | 9 |
| ClaI | 4 | PvuII | 11 |
| EcoRI | 1 | SacI | 10 |
| EcoRV | 2 | SalI | 23 |
| HindIII | 0 | SphI | 9 |
| HpaI | 0 | StuI | 9 |
| KpnI | 5 | XbaI | 0 |
| MluI | 4 | XhoI | 6 |
| NaeI | 14 | | |

[a]number of sites is minimum number determined by counting of fragments visible on gel. It should be noted that smaller fragments (<500 bp) will not be observable when number of bands on gel exceeds ~10-15. Even with few fragments, DNA smaller than 100-200 bp will still not be observed Table II substantially shows the locations of various restriction endonuclease sites in pYO33.

TABLE II

| Restriction Endonuclease | Location (kbp) | Restriction Endonuclease | Location (kbp) |
|---|---|---|---|
| EcoRI | 0 | BglII | 15.8 |
| ClaI | 0.7 | MluI | 17.9 |
| MluI | 1.9 | BglI | 18.2 |
| BglII | 4.8 | KpnI | 18.3 |
| KpnI | 7.0 | BglII | 18.7 |
| EcoRV | 11.2 | ClaI | 18.7 |
| KpnI | 11.4 | KpnI | 20.8 |
| KpnI, ClaI | 13.1 | EcoRV | 26.0 |
| MluI | 13.4 | ClaI | 26.1 |
| MluI | 14.2 | MluI | 33.4 |
| BglII | 14.3 | | |

In the above context, by "substantially" is meant (i) that the relative positions of the restriction sites are substantially accurate based upon the methodology used to generate Table I and Table II, (ii) that one or more restriction sites can be lost or gained by mutations not otherwise significantly affecting the plasmid, and (iii) that additional sites, including sites for enzymes listed in Table I and sites for enzymes not tested, are likely to exist. The restriction enzymes used herein are commercially available. All are described by Roberts, *Nucl. Acids. Res.* 10(5): r117 (1982).

pYO33 was deposited in a strain of V33 in accordance with the Budapest Treaty, and United States Patent and Trademark Office and European Patent Office regulations, in the Agricultural Research Service Culture Collection in Peoria, Illinois, U.S.A. ("ARSCC") on June 22, 1983, under accession number NRRL 15447.

A genetically engineered derivative vector comprising a portion of a naturally occurring plasmid or derivative vector of the invention can be constructed by ligating a functional region of a naturally occurring plasmid of this invention, such as a replicon, to other DNA molecules. Such functional regions can be isolated from a naturally occurring plasmid or derivative vector of this invention by known techniques including, for example, digesting the plasmid or vector with one or more restriction endonucleases to select a particular fragment or to scramble fragments of the plasmid or vector. A functional region of a naturally occurring plasmid or derivative vector of this invention can be ligated, by conventional techniques, to other DNA molecules such as, a replicon for another organism, or a gene expression unit which expresses a desired product, thereby producing a genetically engineered derivative vector. Such a derivative vector can be used as a cloning or expression vector in any strain of Nocardia, including *N. orientalis*. The higher copy number of pYO33 makes it especially useful for overproduction of desired gene products. Products which can be expressed include antibiotics as well as other products naturally made in prokaryotic and eukaryotic systems, including mammalian cells.

Vector pJW7 is an example of a genetically engineered derivative vector of this invention. It contains most of the pYO33 replicator region as well as both the gene for thiostrepton resistance (Ts$^r$) and the gene for melanin production (mel+). pJW7 was constructed by mixing partially Sau3A-digested pYO33 DNA with purified BamHI fragments isolated from pBTM7 DNA, ligating the restriction fragments in the mixture, transforming NRRL 2452 with the ligated mixture, selecting for transformants expressing both the Ts$^r$ and mel+ genes, and isolating the plasmid from such transformants. pBTM7 contains a DNA fragment which carries both the Ts$^r$ and the mel+ genes, and was constructed by ligating partially BclI-digested pBT1 with the BclI fragment of pIJ702 containing the mel+ gene. pIJ702 is a recombinant plasmid found in *Streptomyces lividans* 3131 which is described by Katz et al., *J. Gen. Micro,* 129, 2703–2714 (1983). pBT1 was constructed by inserting the 1.1 kb BamHI fragment from pIJ6 carrying the Ts$^r$ gene into the BamHI site of pBR322. pIJ6 is described by Thompson et al., *Nature,* 186, 525–527 (1980). pBR322 may be isolated by conventional techniques from *E. coli* RRI which is publicly available from several sources, such as the American Type Culture Collection, Rockville, Md., under the accession number ATCC 37017.

pJW7 is approximately 7.1 kb. An illustrative restriction site map of pJW7 is presented in FIG. 2(a). An illustrative restriction site map of the pJW7 replicon is presented in FIG. 1(b). Transformation of a host microorganism, such as NRRL 2452NV1 (i.e. NRRL 2452 cured of its naturally occurring plasmid, pSO408, by treatment with novobiocin), with pJW7 appears to require the presence of a naturally occurring plasmid of this invention (e.g. pSO408) to effect stable, autonomous replication of pJW7 in the transformed host, but such transformants express both the Ts$^r$ and mel+ genes. Thus, pJW7 is a defective vector, i.e., a vector that is lacking in certain replication function(s), requiring that a function be provided in trans for autonomous replication. In a preliminary experiment, the naturally occurring white variant of NRRL 2450, 406W, was not successfully transformed with a pJW7 plasmid preparation that also contained considerably less pSO408 DNA as compared to pJW7 DNA, probably because of restriction by the host. However, if a larger ratio of pSO408 DNA:pJW7 DNA is employed, or if a 406W host containing pSO408 or pYO33 is employed, successful transformation of 406W with pJW7 is expected. Thus, the replicator region of pJW7 is useful for construction of plasmid vectors provided the lacking replication function is provided.

Vector pJW7 is a genetically engineered derivative of pYO33 which has a mutant mel gene which expresses in NRRL 2452NV1. Melanin production is not normally exhibited by NRRL 2452NV1 host transformed with a genetically engineered derivative plasmid of pYO33 containing the mel gene. Thus, it is believed that the mel+ expressed by NRRL 2452NV1 transformed with pJW7 does not result from wild-type mel gene, but instead results from a spontaneous mutation of the wild-type mel gene in the plasmid. pJW7-like vectors can also be obtained by scrambling pJW8D to obtain a plasmid which requires a trans-acting genetic function produced by pSO408 or derivatives thereof for the replication and/or maintenance of pJW7.

Vector pJW8 is another genetically engineered derivative vector of a naturally-occurring vector of this invention. It contains the pYO33 replicon and both the Ts$^r$ and mel+ genes. pJW8 was constructed by the same procedure as used to prepare pJW7, except that it was isolated intact from transformants expressing only the Ts$^r$ gene. pJW8 is reproducibly obtained when prepared according to the aforementioned procedure.

pJW8 is approximately 10.1 kb. An illustrative restriction site map of pJW8 is presented in FIG. 2(c). An illustrative restriction site map of the pJW8 replicon is presented in FIG. 1(c). Transformation of a host microorganism with pJW8 does not appear to require the presence of a naturally occuring plasmid or derivative vector of this invention (i.e. pSO408 or pYO033) to effect stable, autonomous replication of pJW8 in the transformed host. In fact, pJW8 is incompatible with pSO408. pJW8 transformants of NRRL 2452 no longer contain pSO408. Transformation of NRRL 2452 with pJW8 produces transformants that express only the Ts$^r$ gene, while transformation of 406W, the naturally occurring white variant of NRRL 2450, with pJW8 produces transformants that express both the Ts$^r$ and mel+ genes. Since 406W is a naturally occurring variant of NRRL 2450, it can be reliably isolated from cultures of NRRL 2450 by conventional techniques.

Vector pJW8D is a mutant derivative of pJW8, and therefore a derivative of pYO33, which was isolated by visual selection of a colony of 406W transformed with pJW8 which exhibited enhanced production of melanin as compared to 406W containing pJW8.

Transformation of NRRL 2452NV1 with pJW8D produced transformants that expressed both the Ts$^r$ and mel+ genes. As stated earlier, melanin production is not normally exhibited by a NRRL 2452NV1 host transformed with a genetically engineered derivative plasmid of pYO33 containing the mel gene. Thus, the mel+ expressed by NRRL 2452NV1 transformed with pJW8D results from a spontaneous mutation of the wild type mel gene in the plasmid. Retransformation of 406W with pJW8D produced transformants that expressed the Ts$^r$ gene and overexpressed the mel+ gene.

Vector pJW81 is a genetically engineered derivative vector of pYO33 and was produced by digesting pJW8 with StuI and ClaI. Then a 4.5 kb StuI fragment was purified and ligated with an EcoRI fragment (with EcoRI ends filled in with T$_4$ DNA polymerase) derived from pDXT-4 which carries the Ts$^r$ gene. pDXT-4 is pDHX-1 with a BclI fragment from pBT-1 carrying the Ts$^r$ gene inserted into the BclI site of the polylinker. pDHX is a pBR322 plasmid with a polylinker region inserted into the EcoRI site. pJW81 is approximately 6 kb. pBT1 was constructed by inserting the 1.1 kb BamHI fragment from pIJ6 carrying the Ts$^r$ gene into the BamHI site of pBR322. pIJ6 is described by Thompson et al., *Nature,* 186, 525–527 (1980). An illustrative restriction site map of pJW81 is presented in FIG. 3(a). Transformation of NRRL 2452NV1 with pJW81 produced transformants that expressed Ts$^r$.

Figure 3B:
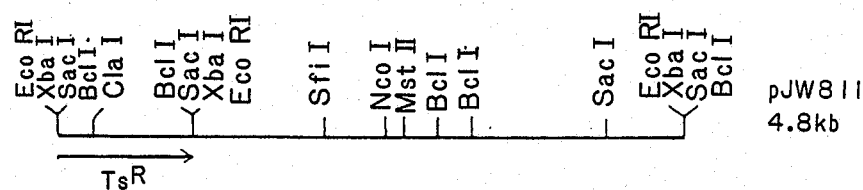
FIG. 3(b) is a restriction endonuclease cleavage map of pJW811.

Vector pJW811 is a genetically engineered derivative of pYO33 and was produced by ligating pJW81 partially digested with BclI and completely digested with BglII with a BclI fragment of pJW7 carrying the mel+ gene. pJW811 is approximately 4.8 kb. An illustrative restriction site map of pJW811 is presented in FIG. 3(b). Transformation of NRRL 2452NV1 with pJW811 produced transformants that expressed Ts$^r$, but not mel+.

Figure 3C:
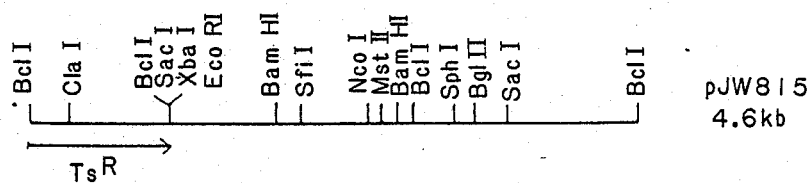
FIG. 3(c) is a restriction endonuclease cleavage map of pJW815.

Vector pJW815 is another genetically engineered derivative of pYO33 and was produced by the same procedure used to prepare pJW811, and was chosed for its reduced size. pJW815 is approximately 4.6 kb. An illustrative restriction site map of pJW815 is presented in FIG. 3(c). Transformation of NRRL 2452NV1 with pJW815 produced transformants that expressed Ts$^r$, but not mel+.

Vector pJW817 is another genetically engineered derivative of pYO33 and was produced by the same procedure used to prepare pJW811, and was chosen because it is smaller than pJW81. pJW817 is approximately 4.8-5 kb. An illustrative restriction site map of pJW817 is not presented because although the plasmid's digestion pattern of several restriction endonucleases has been determined, an insufficient number of different enzymes have been employed to definitively map the plasmid. Transformation of 2452NV1 with pJW817 produced transformants that expressed Ts$^r$, but not mel+.

Figure 3D:
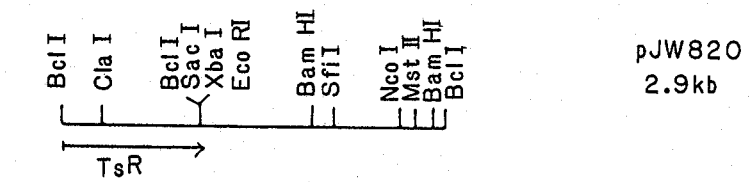
FIG. 3(d) is a restriction endonuclease cleavage map of pJW820.

Vector pJW820 is a genetically engineered derivative of pYO33 and was produced by ligating pJW815 DNA digested with BclI and SphI. pJW820 is approximately 2.9 kb. An illustrative restriction site map of pJW820 is presented in FIG. 3(d). Transformation of NRRL 2452NV1 with pJW820 produced transformants that expressed Ts$^r$, but not mel+.

Figure 3E:
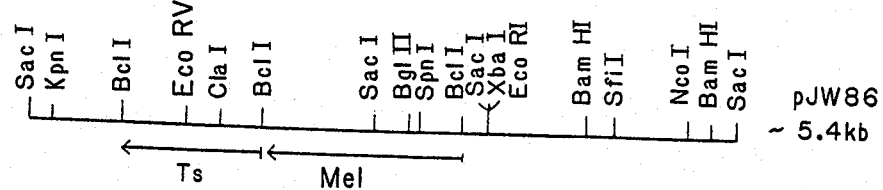
FIG. 3(e) is a restriction endonuclease cleavage map of pJW86.

Vector pJW86 is a genetically engineered derivativere of pYO33 and was produced by ligating pJW8D DNA cut with StuI and SfiI to pJW820 DNA cut with BclI (and ends filled in) and ClaI. pJW86 is approximately 5.4 kb. An illustrative restriction site map of pJW86 is presented in FIG. 3(e). Transformation of NRRL 2452NV1 with pJW86 produced transformants that expressed Ts$^r$ and mel+.

Vector pJW81EM is an example of a genetically engineered derivative of pYO33, and was produced by ligating pJW81 DNA (partially-digested with EcoRI and completely digested with BlII) to pBRE DNA cut with EcoRI, BamHI, and NdeI. pBRE was constructed by cutting pBRLP-1 with XhoI and BglII, and inserting therein a XhoI-BglII fragment from pIJ43 containing a Em$^r$ gene (erythromycin resistance). pIJ43 is described by Thompson et al., *J. Bacteriol.* 151, 678-685 (1983). pBRPL-1 was constructed by cutting pDHB-14 with PstI and closing. pDHB-14 was constructed by the sequential addition of several linkers (commercially available) into pBR322 cut with EcoRI (ends filled in) to form a pBR322 plasmid with a polylinker region (including EcRI sites) with the following restriction endonuclease site order: EcoRI, XbaI, SacI, BclI, XhoI, PvuII, BglII, PstI, BglII, PvuII, XhoI, BclI, SacI, XbaI, EcoRI. pJW81EM is approximately 9 kb. Transformation of NRRL 2452NV1 with pJW81EM produced transformants that expressed Ts$^r$ and Em$^r$. pJW81Em was isolated from such transformants, and the plasmid's digestion pattern of several restriction endonucleases was determined. Such enzyme digestion patterns confirmed the presence of the Em$^r$ gene is such plasmid. However, an insufficient number of different enzymes were employed to definitively map the plasmid.

Em$^r$-containing derivatives of pJW7 were constructed as examples of the use of this vector for cloning. A Em$^r$ fragment, derived by digestion of pDBE-2 using EcoRI, SacI, BamHI, or EcoRI (with ends filled in), was inserted by ligation to pJW7 DNA cut with EcoRI, SacI, BamHI (partially) or StuI, (respectively), and the resulting fragments were then cut with NdeI. Expression of Em$^r$ and Ts$^r$ by host NRRL 2452 cells transformed with such Em$^4$-pJW7 vectors was observed. The Em$^r$-pJW7 vectors were isolated from such transformants by known techniques and their enzyme digestion pattern confirmed the presence of the Em$^r$ gene in such vectors. The plasmid Em$^r$-pJW7 DNA was found to contain simple inserts of the Em$^r$ fragment in the sites indicated by the arrows in FIG. 2(a). pDBE-2 is a derivative of pBRE which has the polylinker region of pDHB-14 (described above) from the BglII site to the NdeI site (including ampicillin resistance-Ap$^r$) replacing the BglII-NdeI portion of pBRE (described above).

Similarly, using conventional techniques, other genetically engineered derivatives of the naturally occurring plasmids and derivative vectors of this invention can be prepared. Derivatives can also be prepared by addition, substitution or deletion of one or a few base pairs such that the function of the resulting derivative vector is not significantly diminished. Techniques for preparing such derivatives include random induced mutagenesis and site directed mutagenesis such as disclosed by Courtney et al., *Nature* 313, 149-151 (1983).

This invention also relates to a host microorganism transformed with a naturally occurring plasmid or other derivative vector of this invention, provided that the host microorganism is other than the natural host for the plasmid. Suitable host microorganisms for the plasmids and derivative vectors of this invention can be determined by conventional techniques, and include other prokaryotes, yeasts, and higher eukaryotes. Preferred host microorganisms include the actinomycetes, especially any strain belonging to the genus Nocardia.

By the term "Nocardia" is meant any actinomycete which can be distinguished from other morphologically similar actinomycetes by its cell wall composition, i.e., a Nocardia cell wall must have meso-diaminopimelic acid plus galactose and arabinose. Such cell wall analysis may be run on either whole-cell hydrolysates or pure cell wall preparations. Other amino acids and sugars such as aspartic acid, glutamic acid, alanine, glucosamine, muramic acid, glucose, mannose, ribose, rhamnose and ribose may also be present as Nocardia cell wall components, since these are non-characterizing components found in all actinomycete genera. L-diaminopimelic acid or xylose and madurose are not Nocardia cell wall components. Thus, as used herein, the term "Nocardia" includes those organisms which are presently classified in another actinomycete genus such as Streptomyces, but which in fact have the characteristic cell wall components of the genus Nocardia.

Preferred Nocardia host microorganisms are those which are glycopeptide antibiotic producers such as the *Streptomyces* (Nocardia) *canadidus* strains which produce the closely related group of factors of glycopeptide antibiotics known as A-35512; the *Streptomyces* (Nocardia) *candidus* strains which produce the glycopeptide antibiotic known as ristocetin; the *Streptomyces* (Nocardia) *eburosporeus* strains which produce the glycopeptide antibiotics known as actinoidin A and B; the *Streptomyces* (Nocardia) *haranomachiensis* strains which produce the glycopeptide antibiotic known as vancomycin; and any other strains of Nocardia which produce vancomycin. Vancomycin-producing Nocardia are the more preferred host microorganisms, and of these *Nocardia orientalis* is the most preferred. The most preferred *Nocardia orientalis* host microorganisms are NRRL 2452, NRRL 2451 and NRRL 2450, especially NRRL 2452 and NRRL 2450.

A suitable host organism can be transformed with any naturally occurring plasmid or derivative vector of this invention by a variety of known techniques, for example, by the method of Chater et al., *Curr. Top. Microbiol. Immunol.* 96: 69-95 (1982), or Bibb et al., *Nature* 274: 398-400 (1978). If desired, a derivative vector of this invention may contain DNA from a phage, and such vector can be cloned into Nocardia by conventional techniques, for example, by the method of Suarez et al., *Nature* 286: 527-529 (1981).

*N. orientalis* strain NRRL 2452 appears to have a SacII-like restriction modification system, that is, SacII sites appear to be methylated so that they are not recognized by SacII restriction endonuclease. Thus, pSO408 and pYO33 are not cut by SacII. However, after ligating the pSO408 or pYO33 plasmid to a vector carrying an *E. coli* replicon and cloning the hybrid in *E. coli*, the pSO408 or pYO33 DNA is restricted by SacII. Therefore, when cloning in *N. orientalis* strain NRRL 2452 and other strains having such SacII-like restriction modification system, it is preferred that other DNA molecules ligated to the plasmids and derivative vectors of this invention, or functional regions thereof, not contain available SacII sites. For example, the fragment carrying thiostrepton resistance from *Streptomyces azureus* has SacII sites while the fragment carrying neomycin resistance from *S. fradiae* does not. See, Thompson et al, *Nature* 286: 525-527 (1980). It is interesting to note that NRRL 2450 has no SacII-like restriction modification system.

If a DNA molecule which is ligated to a naturally occurring plasmid or derivative vector of the invention, or functional region(s) thereof, has a SacII site, or if such derivative is cloned in a host not having such SacII restriction-modification system, the SacII sites in the derivative could be modified prior to cloning in strains having the SacII restriction modification system.

This invention also relates to the expression of a functional DNA sequence derived from Nocardia, other actinomycetes, viruses, other organisms or cells which comprises (a) transforming a host microorganism or cell with a naturally occurring plasmid or derivative vector of this invention which also contains the functional DNA sequence; and (b) culturing the transformed host in an appropriate medium, i.e., a medium which enables the functional DNA sequence to be expressed. The functional DNA sequence can be attached to a naturally occurring plasmid or derivative vector of this invention by ligating the desired functional DNA sequence to such plasmid or vector by conventional techniques. Expression of the desired DNA sequence can be accomplished by transforming a host microorganism with a naturally occurring plasmid or derivative vector of this invention which contains the functional DNA sequence, and then culturing the transformant in an appropriate culture medium, i.e., a culture medium in which the host organism will grow, and which enables the expression of the functional DNA sequence. For example, if a Nocardia host microorganism is transformed with a naturally occurring plasmid or derivative vector of this invention which also contains a functional DNA sequence coding for the production of a polypeptide, such as a sequence coding for the production of insulin, interferon, growth hormone, etc., and the transformed host is then cultured in the appropriate medium, expression of the desired polypeptide product by the transformed Nocardia host will occur. Likewise, if a Norcardia host microoganism is transformed with a plasmid or derivative vector of this invention which contains a functional DNA sequence coding for antibiotic resistance, and the transformed host is then cultured in the appropriate medium, such as a medium which will allow the host to grow and which also contains the antibiotic, expression of the functional DNA sequence by the transformed host will occur and will be evidenced by the ability of the transformed host to grow in the antibiotic-containing culture medium.

By "functional DNA sequence" is meant any discrete region of DNA, which functions, for example, as a complete gene expression unit, as a structural gene, as a promoter and/or regulatory region, as an enhancer sequence, as a signal sequence, or as any other type of functional sequence. By "complete gene expression unit" is meant a structural gene and the promoter and regulatory regions required for its transcription and translation. By "structural gene" is meant a coding sequence which serves as a template for synthesis of messenger RNA. By "promoter" is meant any region upstream of a structural gene which permits binding of RNA polymerase and transcription of a structural gene. By "signal sequence" is meant a sequence which enables secretion of the product of a structural gene. By "enhancer sequence" is meant a sequence which increases transcription. By amplifying gene copy number or plasmid copy number, expression is increased. If the desired functional DNA sequence is simply a structural gene, it can be expressed in a host microorganism transformed therewith by fusing it to its natural promoter, a heterologous promoter derived from a species of the same genus as the host or derived from the source of the DNA sequence, or any other heterologous promoter which is derived from related organisms or produced from synthethic oligonucleotides and which functions in the host. Similarly, appropriate regulatory regions and/or enhancer sequences, either the natural regulatory regions and/or enhancer sequences or functional heterologous regions, can also be fused to the functional DNA sequences as necessary or desired. Preferred functional DNA sequences are those which code for antibiotic resistance, antibiotic production, pigment formation, enzyme production or the production of polypeptides of pharmaceutical importance, e.g., insulin, growth hormones, tissue Plasminogen, Activator, lymphokines, Tumor Necrosis Factor, viral antigens including Heptatitis B Surface Antigen (HBsAg), and protein products.

The method of the subject invention enables one skilled in the art to clone and express in a host microorganism or cell functional DNA sequences derived from Nocardia, other actinomycetes, viruses, or other organisms or cells. Thus, as discussed above, by the method of the subject invention, one can clone genes involved in production of a desired polypeptide on a naturally occurring plasmid or derivative vector of this invention, and use the plasmid to transform a host Nocardia organism that doesn't produce that particular polypeptide in large amounts, thereby providing a system which produces larger quantities of the desired product. Also, by the method of the subject invention, one can clone genese involved in antibiotic biosynthesis in a foreign Nocardia strain or another actinomycete, such as Streptomyces, on a naturally occurring plasmid or derivtive vector of this invention and use it to transform a host Nocardia microorganism that doesn't produce that particular antibiotic, thereby providing a system which produces the antibiotic when the transformed Nocardia host is cultured in the appropriate media. Also, by the method of the subject invention, one can clone genes involved in antibiotic biosynthesis on a naturally occurring plasmid or derivative vector of this invention, and use it to transform a host Nocardia microorganism that already does produce that particular antibiotic, thereby providing a system which can produce increased yields of the antibiotic or altered forms of the antibiotic.

Mutants of the naturally occurring plasmids and derivative vectors of this invention which are able to be stably maintained, extrachromosomally, when transformed into a host microorganism, can be obtained sontaneously or prepared by conventional techniques, such as those described by Davis et al., "Advanced Bacterial Genetics", Cold Spring Harbor (1980) and Miller, "Experiments in Molecular Genetics", Unit III "Mutagenesis and Isolation of Mutants, Cold Spring Harbor (1972).

EXAMPLES

In the following examples, specific embodiments of the invention are more fully disclosed. These examples are intended to be illustrative of the subject invention and should not be construed as limiting its scope. In all examples, temperature is in degrees Centigrade (°C.).

EXAMPLE 1

ISOLATION OF pSO408

The procedure used to isolate pSO408 is substantially as described by Birnboim et al., Nucl. Acids Res. 7: 1513-1523 (1979). N. orientalis strain NRRL 2452, grown for 24 hours (hr) in 2% glycine-trypticase soy broth (TSB), was washed with 10 mM tris-HCl buffer (pH 8.0) containing 10 mM EDTA. The cells were resuspended in 25 mM tris-HCl buffer (pH 8.0) containing 10 mM EDTA, 1% (50 mM) glucose and 20 mg/ml lysozyme. After 1 hr on ice, the mixture was added to 0.2M NaOH-1% sodium dodecyl sulfate (SDS). After 5 minutes (min) on ice, the mixture was transferred into 3M sodium acetate (pH 4.8) and mixed well. After about 1 hr, the mixture was centrifuged and DNA was precipitated from the supernatant with ethanol. pSO408 was then isolated by $CsCl_2$-ethidium bromide density gradient centrifugation as a distinct band.

EXAMPLE 2

PREPARATION OF pYO33 pYO33 was isolated from an arsenate-stressed (i.e. >10 mM sodium arsenate in yeast malt extract agar) strain of NRR1 2452 substantially by the procedure of Example 1, above.

EXAMPLE 3

COSMID CLONING OF pYO33 IN E. COLI

To clone pYO33 in its entirety, a cosmid cloning vector, pJW356, was employed. pJW356 was constructed by fusing pDPT6 cut with PstI, to pIJ350 cut with PstI. pIJ350 is described in Kieser et al., Mol. Gen. Genet., 185, 223-238 (1982). pDPT6 is a tetracycline and chloramphenicol resistant, pBR322-based E. coli cosmid cloning vector described in Taylor et al., U.S. Pat. No. 4,476,227. pJW356 has a unique EcoRI site in the chloramphenicol resistance gene and pYO33 also has a unique EcoRI site, permitting the two plasmids to be fused forming a chimera of about 44 kb which is suitable for packaging in vitro.

One ug of pJW356 cut with EcoRI and 4 ug of pYO33 cut with EcoRI were ligated together in 10 ul with about 200 units of T4 DNA ligase (New England Biolabs) in the recommended buffer, overnight at 16°. The ligated DNA was packaged in vitro using λ extracts. The packaged DNA was used to transfect E. coli strain HB101. After adsorption (15 min. at 37°), the transfected cells were diluted ten fold, incubated for 20 min at 37° and then plated for tetracycline resistant colonies. Chloramphenicol sensitive colonies were identified by screening and examined for plasmid DNA. The resulting plasmid was a hybrid plasmid comprising a fusion of pJW356 and pYO33. Attempts to transform the hybrid plasmid back into N. orientalis strain NRRL 2452 without first modifying the SacII sites were unsuccessful. Attempts to transform the hybrid plasmid back into N. orientalis strain NRRL 2450 and S. lividans 1326 were unsuccessful due to host restriction of the E. coli DNA.

EXAMPLE 4

PREPARATION OF pJW7 pJW7 is a genetically engineered derivative vector of pYO33 comprising most of the pYO33 replicator region and both the $Ts^r$ and mel+ genes. It was constructed by mixing partially Sau3A-digested pYO33 DNA with a purified BamHI fragment from pBTM7, ligating the restriction fragments in the mixture containing 1 ug of each DNA by incubating overnight at 15° with 1 unit of $T_4$ DNA ligase, transforming NRRL 2452 with the ligated mixture by the procedure of Thompson et al., Current Topics in Immunonology and Microbiology, 96, 69-95 (1982), selecting for transformants expressing both the $Ts^r$ and mel+ genes by plating on R2YE plates (see, Thompson et al., cited above) and overlaying with thiostrepton 10 ug/ul final) after 18 hours at 28°, and isolating the plasmid from such transformants by the procedure described by Kieser, Plasmid, 12, 19-36 (1984). pBTM7 is a plasmid which contains both the $Ts^r$ and the mel+ genes, and was constructed by ligating partially BclI-digested pBT1 DNA with the BclI fragment of pIJ702 containing the mel+ gene. pIJ702 is a naturally occurring plasmid found in S. lividans 3131. S. lividans 3131 was obtained from Edward Katz, Department of Microbiology, Georgetown University Schools of Medicine and Dentistry, 3900 Reservoir Road, N.W., Washington, D.C. 20007, U.S.A. pBT1 was constructed by inserting the 1.1 kb BamHI fragment of pIJ6 carrying the $Ts^r$ gene into the BamHI site of pBR322 (ATCC 37017). pIJ6 is described by Thompson, et al., Nature, 186, 525-527 (1980).

pJW7 is not always obtained when one attempts to prepare it according to the aforementioned procedure because melanin production does not result from wild-type mel gene (as in pJW8) but instead results from a spontaneous mutation. pJW7-like plasmids can also be obtained by scrambling pJW8D to obtain a plasmid which requires a trans-acting genetic function produced by pSO408 or derivatives thereof for the replication and/or maintenance of pJW7 since pJW7 appears not to contain such essential function.

EXAMPLE 5

TRANSFORMATION OF NRRL 2452 WITH pJW7

NRRL 2452 protoplasts were transformed with pJW7. The protoplasts were prepared by the method of Example 1, i.e. by growth in 2% glycine-TSB and treatment with 20 mg/ml lysozyme in P medium [See, Thompson et al., *Current Topics in Immunonology and Microbiology*, 96, 69-95 (1982)]. Transformation was effected by the method of Thompson et al, cited above.

EXAMPLE 6

DETECTION OF NRRL 2452 HOSTS TRANSFORMED WITH pJW7 AND EXPRESSION OF A FUNCTIONAL DNA SEQUENCE

Transformants, prepared as described in Example 5, expressed both the Ts$^r$ and mel+ genes, and were detected by their ability to grow and form colonies in the presence of thiostrepton and their ability to produce brown melanin pigment which was excreted in the agar around the colonies.

EXAMPLE 7

TRANSFORMATION OF NRRL 2452NV1 WITH pJW7

NRRL 2452NV1 (cured NRRL 2452) was derived from the original transformant of NRRL 2452 containing the pJW8 vector by the following method: The original transformant was inoculated into 50 ml TSB and allowed to grow overnight. Then, the culture was subcultured into TSB-containing 0.39 ug/ml novobiocin and incubated for 3 days. Then, the subcultures were subcultured again into TSB-containing 12.5 ug/ml novobiocin and incubated for 3 days. Dilutions of these subcultures were plated on R2YE plates, and the colonies formed were tested for Ts$^r$. 95% of such colonies were sensitive to thiostrepton (Ts$^s$). Such Ts$^s$ colonies were checked for presence of plasmid, and no visible pSO408, pYO33 or pJW8 was found. To confirm the absence of plasmid, nick-translated pYO33 was used to probe for plasmid by Southern hybridization, and no plasmid was detected. Such cured colonies were designated as NRRL 2452NV1.

NRRL 2452NV1 protoplasts were prepared and transformed with pJW7 DNA containing some pSO408 DNA according to the method of Example 5.

EXAMPLE 8

DETECTION OF NRRL 2452NV1 HOSTS TRANSFORMED WITH pJW7 AND EXPRESSION OF A FUNCTIONAL DNA SEQUENCE

Transformants, prepared according to the method of Example 7, expressed both the Ts$^r$ and mel+ genes, and were detected by the method of Example 6.

Transformation of NRRL 2452NV1 with pJW7 appears to require the presence of a naturally occurring plasmid of this invention, i.e. pS0408, or a derivative vector thereof, i.e., pYO33, to effect stable, autonomous replication of pJW7 in the transformed NRRL 2452NV1 host. This result indicates that pJW7 requires a trans-acting genetic function produced by pSO408 or derivatives thereof for the replication and/or maintenance of pJW7 since pJW7 appears not to contain such essential function. In a preliminary experiment, 406W, the naturally occurring white variant of NRRL 2450, was not successfully transformed with a pJW7 plasmid preparation that also contained considerably less pSO408 DNA as compared to pJW7 DNA, probably because of restriction by the host. However, if a larger ratio of pSO408 DNA:pJW7 DNA is employed, or if a 406W host containing pSO408 or pYO33 is employed, successful transformation of 406W with pJW7 is expected.

EXAMPLE 9

PREPARATION OF pJW8 pJW8 is a genetically engineered derivative vector of pYO33 comprising the pYO33 replicon and both the Ts$^r$ and mel+ genes. It was constructed according to the method of Example 4 and was detected by selecting for transformants exhibiting Ts$^r$. Screening of Ts$^r$ transformants [using the mini-prep procedure described by Kieser et al., *Mol. Gen. Genet.*, 185, 223-238 (1982) or Birnboim et al., *Nucl. Acids Res.* 7, 1513-1523 (1979)] revealed a family of plasmids, and pJW8 was chosen for its reduced size as determined by agarose gel electrophoresis.

EXAMPLE 10

TRANSFORMATION OF NRRL 2452 WITH pJW8

NRRL 2452 protoplasts were prepared and transformed with pJW8 according to the method of Example 5.

EXAMPLE 11

DETECTION OF NRRL 2452 HOSTS TRANSFORMED WITH pJW8 AND EXPRESSION OF A FUNCTIONAL DNA SEQUENCE

Transformants, prepared according to the method of Example 10, expressed only the Ts$^r$ gene, and were detected by their ability to grow and form colonies in the presence of thiostrepton. The plasmid's presence was confirmed by isolating the plasmid from the transformed host by the method of Example 4, and producing an enzyme digestion pattern according to conventional techniques.

EXAMPLE 12

TRANSFORMATION OF NRRL 406W WITH pJW8

Protoplasts from 406W were prepared, and then transformed with pJW8, according to the method of Example 5.

EXAMPLE 13

DETECTION OF 406W HOSTS TRANSFORMED WITH pJW8 AND EXPRESSION OF A FUNCTIONAL DNA SEQUENCE

Transformants expressed both the Ts$^r$ gene and the mel+ gene and were detected by the method of Example 6. The plasmid's presence was confirmed by the method of Example 11.

EXAMPLE 14

PREPARATION OF pJW8D pJW8D is a mutant derivative of pJW8 which was produced spontaneously and identified in 406W as an enhanced producer of melanin as compared to 406W carrying pJW8.

EXAMPLE 15

TRANSFORMATION OF NRRL 2452NV1 WITH pJW8D

NRRL 2452NV1 protoplasts were prepared and transformed with pJW8D according to the method of Example 5.

EXAMPLE 16

DETECTION OF NRRL 2452NV1 HOSTS TRANSFORMED WITH pJW8D AND EXPRESSION OF A FUNCTIONAL DNA SEQUENCE

Transformants, prepared according to the method of Example 15, expressed both the Ts$^r$ and the mel+ genes, and were detected by the method of Example 6. The plasmid's presence was confirmed by the method of Example 11.

EXAMPLE 17

TRANSFORMATION OF 406W WITH pJW8D 406W protoplasts were prepared and transformed with pJW8D according to the method of Example 5.

EXAMPLE 18

DETECTION OF 406W HOSTS TRANSFORMED WITH pJW8D AND EXPRESSION OF A FUNCTIONAL DNA SEQUENCE

Transformants, prepared according to the method of Example 17, expressed the Ts$^r$ gene and overexpressed the mel+ gene, and were detected by the method of Example 6. The plasmid's presence was confirmed by the method of Example 11.

EXAMPLE 19

PREPARATION OF pJW81 pJW81 is a genetically engineered derivative of pJW8 and was produced by digesting pJW8 with StuI and ClaI. Then a 4.5 kb StuI fragment was purified and ligated with an EcoRI fragment (with EcoRI ends filled in with T$_4$ DNA polymerase) derived from a pDXT-4 which carries the Ts$^r$ gene. pDXT-4 is pDHX-1, a pBR322 plasmid with a polylinker region inserted into the EcoRI site, with a BclI fragment from pBT-1 carrying the Ts$^r$ gene inserted into the BclI site of the polylinker. The construction of pBT-1 is described in Example 4.

EXAMPLE 20

TRANSFORMATION OF NRRL 2452NV1 WITH pJW81

NRRL 2452NV1 protoplasts were prepared and transformed with pJW81 according to the method of Example 5.

EXAMPLE 21

DETECTION OF NRRL 2452NV1 HOSTS TRANSFORMED WITH pJW81 AND EXPRESSION OF A FUNCTIONAL DNA SEQUENCE

Transformants, prepared according to the method of Example 21, expressed Ts$^r$, and were detected by the method of Example 11. The plasmid's presence was confirmed by the method of Example 11.

EXAMPLE 22

PREPARATION OF pJW811 pJW811 is a genetically engineered derivative of pJW81 and was produced by ligating pJW81 partially digested with BclI and completely digested with BglII with a BcLI fragment of pJW7 carrying the mel+ gene.

EXAMPLE 23

TRANSFORMATION OF NRRL 2452NV1 WITH pJW811

NRRL 2452NV1 protoplasts were prepared and transformed with pJW811 according to the method of Example 5.

EXAMPLE 24

DETECTION OF NRRL 2452NV1 HOSTS TRANSFORMED WITH pJW811 AND EXPRESSION OF A FUNCTIONAL DNA SEQUENCE

Transformants, prepared according to the method of Example 23, expressed Ts$^r$, and were detected by the method of Example 11. The plasmid's presence was confirmed by the method of Example 11.

EXAMPLE 25

PREPARATION OF pJW815 pJW815 is a genetically engineered derivative of pJW81 and was produced by the same procedure used to prepare pJW811, and was chosen for its reduced size as determined by agarose gel electrophoresis.

EXAMPLE 26

TRANSFORMATION OF NRRL 2452NV1 WITH pJW815

NRRL 2452NV1 protoplasts were prepared and transformed with pJW815 according to the method of Example 5.

EXAMPLE 27

DETECTION OF NRRL 2452NV1 HOSTS TRANSFORMED WITH pJW815 AND EXPRESSION OF A FUNCTIONAL DNA SEQUENCE

Transformants, prepared according to the method of Example 26, expressed Ts$^r$ and were detected by the method of Example 11. The plasmid's presence was confirmed by the method of Example 11.

EXAMPLE 28

PREPARATION OF pJW817 pJW817 is a genetically engineered derivative of pJW81 and was produced by the same procedure used to prepare pJW811, and was chosen for its reduced size as determined by agarose gel electrophoresis.

EXAMPLE 29

TRANSFORMATION OF NRRL 2452NV1 WITH pJW817

NRRL 2452NV1 protoplasts were prepared and transformed with pJW817 according to the method of Example 5.

EXAMPLE 30

DETECTION OF NRRL 2452NV1 HOSTS TRANSFORMED WITH pJW817 AND EXPRESSION OF A FUNCTIONAL DNA SEQUENCE

Transformants, prepared according to the method of Example 29, expressed Ts$^r$, and were detected by the method of Example 11, and the plasmid's digestion pattern of several restriction endonucleases were determined. However, insufficient enzymes have been employed to definitively map the plasmid.

EXAMPLE 31

PREPARATION OF pJW820 pJW820 is a genetically engineered derivative of pJW815, and was produced by ligating pJW815 DNA digested with BclI and SphI.

EXAMPLE 32

TRANSFORMATION OF NRRL 2452NV1 WITH pJW820

NRRL 2452NV1 protoplasts were prepared and transformed with JW820 according to the method of Example 5.

EXAMPLE 33

DETECTION OF NRRL 2452NV1 HOSTS TRANSFORMED WITH pJW820 AND EXPRESSED OF A FUNCTIONAL DNA SEQUENCE

Transformants, prepared according to the method of Example 32, expressed Ts$^r$, and were detected by the method of Example 11. The plasmid's presence was confirmed by the method of Example 11.

EXAMPLE 34

PREPARATION OF pJW86 pJW86 is a genetically engineered derivative of pJW820 and pJW8D and was produced by ligating pJW8D DNA digested with StuI and SfiI to pJW820 DNA cut with StuI (ends filled in) and ClaI.

EXAMPLE 35

TRANSFORMATION OF NRRL 2452NV1 WITH pJW86

NRRL 2452NV1 protoplasts were prepared and transformed with pJW86 according to the method of Example 5.

EXAMPLE 36

DETECTION OF NRRL 2452NV1 HOSTS TRANSFORMED WTIH PJW86 AND EXPRESSION OF A FUNCTIONAL DNA SEQUENCE

Transformants, prepared according to the method of Example 35, expressed Ts$^r$, and were detected by the method of Example 11. The plasmid's presence was confirmed by the method of Example 11.

EXAMPLE 37

PREPARATION OF pJW81EM pJW81EM is a genetically engineered derivative of pJW81 and was produced by ligating pJW81 DNA partially-digested with EcoRI and completely digested with BglII to pBRE DNA cut with BamHI and NdeI. pBRE was constructed by cutting pBRPL-1 with XhoI and BglII, and inserting therein a XhoI-BglII fragment from pIJ43 containing a Em$^r$ gene (erythromycin resistance). pIJ43 is described by Thompson et al, *J. Bacteriol.*, 151, 678–685 (1983). pBRPL-1 was constructed by cutting pDHB-14 with PstI and closing. pDHB-14 was constructed by the sequential addition of several linkers (commercially available) into pBR322 cut with EcoRI (ends filled in) to form a pBR322 plasmid with a polylinker region (including EcoRI sites) with the following restriction endonuclease site order: EcoRI, XbaI, SacI, BclI, XhoI, PvuII, BglII, PstI, BglII, PvuII, XhoI, BclI, SacI, XbaI, EcoRI.

EXAMPLE 38

TRANSFORMATION OF NRRL 2452NV1 WITH pJW81EM

NRRL 2452NV1 protoplasts were prepared and transformed with pJW81EM according to the method of Example 5.

EXAMPLE 39

DETECTION OF NRRL 2462NV1 HOSTS TRANSFORMED WITH pJW81EM AND EXPRESSION OF A FUNCTIONAL DNA SEQUENCE

Transformants, prepared according to the method of Example 38, expressed Ts$^r$ and Em$^r$, and were detected by their ability to grow and form colonies in the presence of thiostrepton and erythromycin. The plasmid's presence was confirmed by the method of Example 11, and the plasmid's enzyme digestion pattern of several restriction endonucleases was determined. Such enzyme digestion patterns confirmed the presence of the Em$^r$ gene in such plasmid. However, insufficient enzymes were employed to definitively map the plasmid.

EXAMPLE 40

PREPARATION OF pJW7 DERIVATIVE VECTORS CONTAINING THE Em$^r$ GENE

Em$^r$-containing derivatives of pJW7 were constructed as examples of the use of this vector for cloning. A Em$^r$ fragment, derived by digestion of pDBE-2 using EcoRI, SacI, BamHI, or EcoRI (with ends filled in), was inserted by ligation to pJW7 DNA out with EcoRI, SacI, BamHI (partially) or StuI, (respectively), and the resulting fragments were then cut with NdeI. Expression of Em$^r$ and Ts$^r$ by host NRRL 2452 cells transformed with such Em$^r$-pJW7 vectors was observed. The Em$^r$-pJW7 vectors were isolated from such transformants by known techniques, and their enzyme digestion pattern confirmed the presence of the Em$^r$ gene in such vectors. The plasmid DNA was found to contain simple inserts of the Em$^r$ fragment in the sites indicated by the arrows in FIG. 2(a). pDBE-2 is a derivative of pBRE which has the polylinker region of pDHB-14 from the BglII site to NdeI site (including Ap$^r$) replacing the BglII-NdeI portion of pBRE. pDHB-14 is described in Example 35.

While the preferred embodiments of the invention are described by the above, the invention is not limited to the precise constructions herein disclosed but rather includes all embodiments and modifications coming within the scope of the following claims.

We claim:

1. Plasmid pSO408, which is naturally present in *N. orientalis* strain NRRL 2452, isolated from such strain, or a functional mutant or genetically engineered derivative thereof wherein said mutant or derivative possesses sufficient amount of the replicon of pSO408 to permit stable autonomous replication.

2. The plasmid of claim 1 which is pSO408.

3. A plasmid of claim 2 which is pYO33, or a functional mutant or genetically engineered derivative thereof.

4. The plasmid of claim 3 which comprises the replicator region of pYO33 or pSO408.

5. The plasmid of claim 4 which is pJW7, pJW8, pJW81, pJW811, pJW815, pJW8D, pJW817, pJW820, pJW86 or pJW81Em, or a functional mutant or genetically engineered derivative thereof.

6. The plasmid of claim 5 which is pJW820.

7. A host microorganism transformed with the plasmid of claim 1, provided that when the plasmid is pSO408, the host is other than *N. orientalis* strain NRRL 2452.

8. A host microorganism transformed with the plasmid of claim 2, provided that the host is other than *N. orientalis* strain NRRL 2452.

9. A host microorganism transformed with the vector of claim 3.

10. A host microorganism transformed with the vector of claim 4.

11. A host microorganism transformed with the vector of claim 5.

12. A host microorganism transformed with the vector of claim 6.

13. The host microorganism of claim 7 wherein such microorganism is naturally capable of producing a peptide-containing antibiotic.

14. The host microorganism of claim 13 wherein the antibiotic is a glycopeptide-containing antibiotic.

15. The host microorganism of claim 14 wherein such host belongs to the species *N. orientalis*.

16. The plasmid of claim 1 which additionally comprises a functional DNA sequence.

17. A host microorganism transformed with the plasmid of claim 16.

UNITED STATES PATENT AND TRADEMARK OFFICE
CERTIFICATE OF CORRECTION

PATENT NO. : 4,791,064

DATED : December 13, 1988

INVENTOR(S) : Louis R. Fare et al.

It is certified that error appears in the above-identified patent and that said Letters Patent is hereby corrected as shown below:

In Claim 3, at column 19, line 9, delete "claim 2 and insert therefor --claim 1--.

Signed and Sealed this

First Day of August, 1989

Attest:

DONALD J. QUIGG

Attesting Officer

Commissioner of Patents and Trademarks